(12) United States Patent
Matringe et al.

(10) Patent No.: US 10,138,490 B2
(45) Date of Patent: Nov. 27, 2018

(54) TRANSFORMED PLANTS TOLERANT TO HERBICIDES DUE TO OVEREXPRESSION OF PREPHENATE DEHYDROGENASE AND P-HYDROXYPHENYLPYRUVATE DIOXYGENASE

(76) Inventors: Michel Matringe, Grenoble (FR); Pascal Rippert, Zurich (CH); Manuel Dubald, Saint Didier Au Mont d'Or (FR); Renaud Dumas, Bourgoin-Jallieu (FR)

( * ) Notice: Subject to any disclaimer, the term of this patent is extended or adjusted under 35 U.S.C. 154(b) by 1112 days.

(21) Appl. No.: 11/078,038

(22) Filed: Mar. 11, 2005

(65) Prior Publication Data

US 2005/0257283 A1     Nov. 17, 2005

Related U.S. Application Data

(63) Continuation of application No. PCT/FR03/02684, filed on Sep. 10, 2003.

(30) Foreign Application Priority Data

Sep. 11, 2002 (FR) .................................. 02 11209

(51) Int. Cl.
    *C12N 15/82*        (2006.01)

(52) U.S. Cl.
    CPC ..... *C12N 15/8243* (2013.01); *C12N 15/8274* (2013.01)

(58) Field of Classification Search
    USPC ........................................................ 800/300
    See application file for complete search history.

(56) References Cited

U.S. PATENT DOCUMENTS

| | | | |
|---|---|---|---|
| 5,188,642 A | 2/1993 | Shah et al. | |
| 5,424,276 A | 6/1995 | Cain et al. | |
| 5,506,195 A | 4/1996 | Ensminger et al. | |
| 5,614,313 A | 3/1997 | Mills et al. | |
| 5,641,876 A | 6/1997 | McElroy et al. | |
| 5,866,778 A | 2/1999 | Hartman et al. | |
| 5,994,521 A | 11/1999 | Maiti et al. | |
| 6,268,549 B1 * | 7/2001 | Sailland et al. | 800/295 |
| 6,624,342 B1 * | 9/2003 | Grimm et al. | 800/278 |
| 7,112,717 B2 * | 9/2006 | Valentin et al. | 800/278 |
| 7,279,302 B2 * | 10/2007 | Matringe et al. | 435/26 |
| 2003/0066102 A1 * | 4/2003 | Maxwell et al. | 800/278 |

FOREIGN PATENT DOCUMENTS

| | | |
|---|---|---|
| EP | 418175 | 3/1991 |
| EP | 470856 | 2/1992 |
| EP | 496630 | 7/1992 |
| EP | 496631 | 7/1992 |
| EP | 0527036 | 2/1993 |
| EP | 0531498 | 3/1993 |
| EP | 0560482 | 9/1993 |
| EP | 0625505 | 11/1994 |
| EP | 0625508 | 11/1994 |
| WO | WO199113993 | 9/1991 |
| WO | WO199217580 | 10/1992 |
| WO | WO199638567 | 12/1996 |
| WO | WO199704103 | 2/1997 |
| WO | WO199730082 | 8/1997 |
| WO | WO199822593 | 5/1998 |
| WO | WO199840490 | 9/1998 |
| WO | WO199845460 | 10/1998 |
| WO | WO199845461 | 10/1998 |
| WO | WO199846763 | 10/1998 |
| WO | WO199846764 | 10/1998 |
| WO | WO199902717 | 1/1999 |
| WO | WO199915679 | 4/1999 |
| WO | WO199916890 | 4/1999 |
| WO | WO199923231 | 5/1999 |
| WO | WO199924585 | 5/1999 |
| WO | WO199924586 | 5/1999 |
| WO | WO199924594 | 5/1999 |
| WO | WO199934005 | 7/1999 |
| WO | WO199943818 | 9/1999 |
| WO | WO199953053 | 10/1999 |
| WO | WO200001833 | 1/2000 |
| WO | WO200008169 | 2/2000 |
| WO | WO200036127 | 6/2000 |
| WO | WO200061771 | 10/2000 |
| WO | WO 2002/046441 * | 6/2002 |
| WO | WO200246441 | 6/2002 |
| WO | WO2002089561 | 11/2002 |
| WO | WO2004024928 | 3/2004 |

OTHER PUBLICATIONS

Mannhaupt et al 1989 Gene 85: 303-311.*
UniProtKB Accession No. P20049 ([online], [retrieved on Jun. 27, 2013], retrieved from the internet <http://www.uniprot.org/uniprot/P20049 >).*
Meazza et al. (The inhibiroty activity of natural products on plant p-hydroxyphenylpyruvate dioxygenase, 59 Phytochemistry, 281-288 (2002)).*
Berg et al. (Biochemistry Section 8.5 (2002); available at http://www.ncbi.nlm.nih.gov/books/NBK22530/).*
Rippert et al. (Molecular and biochemical characterization of an *Arabidopsis thaliana* arogenate dehydrogenase with two highly similar and active protein domains, 48 Plant Molecular Biology, 361-368 (2002).*
Packer et al. 2001, Molecular aspects of alpha-tocotrienol antioxidant action and cell signalling. J. Nutr. 131(2): 3698-3738.
Qureshi et al. 2001, Novel tocotrienols of rice bran inhibit atherosclerotic lesions in C57BL/6 ApoE-deficient mice. J. Nutr. 131: 2606-2618.

(Continued)

*Primary Examiner* — David H Kruse
(74) *Attorney, Agent, or Firm* — Arent Fox LLP

(57) ABSTRACT

The present invention relates to transformed plants, in particular transformed plants producing larger amounts of plastoquinones, tocotrienols and tocopherols than non-transformed identical plants. This invention also relates to a method for producing these plants, and to a method for cultivating these plants. The plants according to the invention also have the property of being tolerant to herbicides that are inhibitors of the p-hydroxyphenylpyruvate dioxygenase enzyme.

17 Claims, 2 Drawing Sheets

(56) References Cited

OTHER PUBLICATIONS

Garcia et al. 1999, Characterization and subcellular compartmentation of recombinant 4-hydroxyphenylpyruvate dioxygenase from *Arabidopsis* in transgenic tobacco. Plant Physiol. 119, 1507-1516.
Brown. 1998, Molecular Biology LabFax, Second edition, Academic Press, UK (Table of Contents).
Keller et al. 1998, Metabolic compartmentation of plastid prenyl-lipid biosynthesis—evidence for the involvement of a multifunctional geranylgeranyl reductase. Eur. J. Biochem. 251(1-2): 413-417.
Viviani et al. 1998, The Mode of Action of Isoxaflutole Pestic. Biochem. Physiol. 62: 125-134.
Garcia et al. 1997, Subcellular localization and purification of a p-hydroxyphenylpyruvate dioxygenase from cultured carrot cells and characterization of the corresponding cDNA. Biochem. J. 325: 761-769.
Smith et al. 1997, The cloning of two *Arabidopsis* genes belonging to a phosphate transporter family. Plant J. 11: 83-92.
Ellis et al. 1996, Characterization of the interaction of 2-[2-nitro-4-(trifluoromethyl)benzoyl]-4,4,6,6,-tetramethyl-cyclohexane-1,3,5-trione with rat hepatic 4-hydroxyphenylpyruvate dioxygenase. Chem. Res. Toxicol. 9: 24-27.
Abou-zeid et al. 1995, Biosynthesis of L-Phenylalanine and L-Tyrosine in the Actinomyces Amycolatopsis methanolica App Envirol Microbiol 61(4):1298-1302.
Bonner et al. 1995, Distinctive Enzymes of Aromatic Amino Acid Biosynthesis That Are Highly Conserved in Land Plants Are Also Present in the Chlorophyte Alga Chlorella sorokiniana. Plant Cells Physiol. 36, 1013-1022.
Cordero et al. 1994, Expression of a maize proteinase inhibitor gene is induced in response to wounding and fungal infection: systemic wound-response of a monocot gene. Plant J., 6 (2) 141-150.
Croy R.D.D. 1993, Plant Molecular Biology LabFax, BIOS Scientific Publications Ltd (UK) and Blackwell Scientific Publications (UK), (Table of Contents).
Schwob et al. 1993, Molecular analysis of three maize 22 kDa auxin-binding protein genes—transient promoter expression and regulatory regions. Plant J. 4 (3): 423-432.
Xia et al. 1992, A monofunctional prephenate dehydrogenase created by cleavage of the 5' 109 bp of the tyrA gene from Erwinia herbicola J. Gen. Microbiol. 138(7), 1309-1316.
Padgette et al. 1991, Site-directed mutagenesis of a conserved region of the 5-enolpyruvylshikimate-3-phosphate synthase active site. J. Biol. Chem. 266: 22364-9.
Xia et al. Submitted Sep. 1991 GenBank Accession: S29934, chorismate mutase (EC 5.4.99.5) / prephenate dehydrogenase (EC 1.3.1.12) tyrA [similarity]—Erwinia herbicola.
Bruce et al. 1989, Photoregulation of a phytochrome gene promoter from oat transferred into rice by particle bombardment. Proc. Natl. Acad. Sci. USA 86(24), 9692-9696.
Mannhaupt et al. 1989, Characterization of the prephenate dehydrogenase-encoding gene, TYR1, from *Saccharomyces cerevisiae*. Gene 85, 303-312.
Martinez et al. 1989, Structure, evolution and anaerobic regulation of a nuclear gene encoding cytosolic glyceraldehyde-3-phosphate dehydrogenase from maize. J. Mol. Biol., 208 (4), 551-565.
Connely et al. 1986, Tyrosine Biosynthesis in Sorghum bicolr: Isolation and Regulatory Properties of Arogenate Dehydrogenase. Z. Naturforsch 41c: 69-78.

\* cited by examiner

TRANSFORMED PLANTS TOLERANT TO HERBICIDES DUE TO OVEREXPRESSION OF PREPHENATE DEHYDROGENASE AND P-HYDROXYPHENYLPYRUVATE DIOXYGENASE

REFERENCE TO RELATED APPLICATIONS

This application is a continuation of International Application PCT/FR03/02684 published in French on Sep. 10, 2003 claiming priority of French application 0211209 filed on Sep. 11, 2002, each of which is incorporated herein by reference in its entirety.

FIELD OF THE INVENTION

This invention relates to transformed plants that express plastoquinones, tocotrienols and tocopherols, and methods for making such plants.

BACKGROUND OF THE INVENTION

Prenylquinones are a large group of compounds with lipid affinities comprising, inter alia, plastoquinones, tocopherols and tocotrienols. In plants, prenylquinones are synthesized via the homogentisate pathway.

The most well-known prenylquinone is vitamin E, or α-tocopherol, an essential element of the human or animal diet, in particular that of mammals which do not produce it naturally but have a dietary need thereof. The most recognized effect of vitamin E is its antioxidant action on cell membrane lipids (Epstein et al., 1966, Radical Research 28: 322-335; Kamel-Eldin and Appelqvist, 1996, Lipids 31: 671-701).

Other than vitamin E, it has been demonstrated that tocotrienols, although they are not essential in the human and animal diet, have particularly advantageous antioxidant properties that are more pronounced than those of vitamin E (Kamat et al., 1997, Mol. Cell. Biochem. 170, 131-137). These compounds are in particular known to protect cells against free radicals, and also to prevent the appearance of cardiovascular diseases or of cancers (Packer et al., 2001, J. Nutr. 131(2): 369S-373S). In addition, tocotrienols exhibit anticancer activity by inhibition of estrogen receptor proliferation, an activity that tocopherols do not possess (Guthrie et al., 1997, J. Nutr. 127: 544-548). They also exhibit a much better hypocholesterolemic activity than tocopherols (Pearce et al., 1992, J. Med. Chem. 35: 3595-3606; Qureshi et al., 2001, J. Nutr. 131: 2606-2618), which makes them more capable of combating arteriosclerosis.

Plastoquinones have no known role in human or animal health, but play an essential role in plants. These molecules are present in chloroplast membranes and their function is that of electron transport during the photosynthesis reaction (Grumbach, 1984, Structure Function and Metabolism of plant lipids, Siegenthaler and Eichenberger eds.).

In addition, an increase in the amount of prenylquinones should confer on plants better resistance to oxidative stresses, in particular cold, drought or strong light.

In plants and photosynthetic organisms in general, homogentisate constitutes the aromatic precursor of prenylquinones. Homogentisate is the product of the p-hydroxyphenylpyruvate dioxygenase enzyme (hereinafter referred to as HPPD). In most organisms, HPPDs are enzymes involved in the catabolic degradation pathway of the aromatic amino acid tyrosine (Goodwin, 1972, in Tyrosine Metabolism: The biochemical, physiological and clinical significance of p-hydroxyphenylpyruvate oxygenase, Goodwin B. L., ed., Oxford University press, 1-94). HPPDs catalyze the reaction of conversion of para-hydroxyphenylpyruvate (HPP), a tyrosine degradation product, to homogentisate.

Most plants synthesize tyrosine via arrogenate (Abou-Zeid et al. 1995 Applied Env Microb 41: 1298-1302; Bonner et al., 1995 Plant Cells Physiol. 36, 1013-1022; Byng et al., 1981 Phytochemistry 6: 1289-1292; Connely and Conn 1986 Z. Naturforsch 41c: 69-78; Gaines et al., 1982 Plants 156: 233-240). In these plants, the HPP is derived only from the degradation of tyrosine. On the other hand, in organisms such as the yeast *Sacharomyces cerevisiae* or the bacterium *Escherichia coli*, HPP is a tyrosine precursor, and it is synthesized by the action of an enzyme, prephenate dehydrogenase (hereinafter referred to as PDH), which converts prephenate to HPP (Lingens et al., 1967 European J. Biochem 1: 363-374; Sampathkumar and Morrisson 1982 Bioch Biophys Acta 701: 204-211). In these organisms, the production of HPP is therefore directly connected to the aromatic amino acid biosynthetic pathway (shikimate pathway), and not to the tyrosine degradation pathway (see Figure 1).

Up until now, three main strategies using genetic engineering have been employed in order to make plants tolerant to herbicides. The first consists in detoxifying the herbicide by transforming the plant with a gene encoding a detoxifying enzyme. This enzyme converts the herbicide, or its active metabolite, into nontoxic degradation products, for instance the enzymes for tolerance to bromoxynil or to baste (EP 242 236, EP 337 899).

The second strategy consists in transforming the plant with a gene encoding the target enzyme that has been mutated in such a way that it is less sensitive to the herbicide, or its active metabolite, for instance the glyphosate tolerance enzymes (EP 293 356; Padgette et al., 1991, J. Biol. Chem. 266: 33).

The third strategy consists in overexpressing the sensitive target enzyme in such a way as to produce, in the plant, large amounts of target enzyme, if possible much greater than the amount of herbicide entering the plant. This strategy makes it possible to maintain a sufficient level of functional enzyme, despite the presence of its inhibitor. This third strategy has been implemented and has made it possible to obtain plants tolerant to HPPD inhibitors (WO 96/38567). In addition, this simple strategy of overexpression of the sensitive (non-mutated) target enzyme was used successfully for the first time for conferring on plants tolerance at an agronomic level to a herbicide.

It is also known that most HPPD-inhibiting herbicides are competitive inhibitors with respect to the substrate, that bind slowly and virtually irreversibly (Ellis et al., 1996, Chem. Res. Toxicol. 9: 24-27; Viviani et al., 1998, Pestic. Biochem. Physiol. 62: 125-134). Their mode of action therefore consists in competing with the HPP by binding preferentially to its binding site. The result of this binding is an arrest of homogentisate synthesis by the cell.

SUMMARY OF THE INVENTION

The present invention relates to transformed plants, in particular transformed plants producing larger amounts of plastoquinones, tocotrienols and tocopherols than non-transformed identical plants. This invention also relates to a method for producing these plants, and to a method for cultivating these plants. The plants according to the invention also have the property of being tolerant to herbicides that are inhibitors of the p-hydroxyphenylpyruvate dioxygenase enzyme (HPPD).

In order to increase the biosynthesis of prenylquinones by plants, the inventors of the present patent application have sought to increase the flux of the HPP precursor into the cells of these plants by connecting the synthesis of the precursor to the "shikimate" pathway by overexpression of a prephenate dehydrogenase (PDH). The effect is a greater flux of the HPP precursor, which overall, increases prenylquinone biosynthesis.

The transformation of plants with a gene encoding a PDH enzyme increases the production of prenylquinones by the plants. This increase is very significant when the plants transformed with a gene encoding a PDH enzyme are plants that also overexpress an HPPD enzyme.

The transformation of plants with a gene encoding a PDH enzyme increases the tolerance of the plants to HPPD inhibitors. This increase in tolerance is very significant when the plants transformed with a gene encoding a PDH enzyme are plants that also overexpress an HPPD enzyme.

Over the last few years, interest in HPPDs has considerably increased following the demonstration that this enzyme is the target of new families of "bleaching" herbicides. Such herbicides whose target is HPPD are especially isoxazoles (EP 418 175, EP 470 856, EP 487 352, EP 527 036, EP 560 482, EP 682 659, U.S. Pat. No. 5,424,276), in particular isoxaflutole, a selective herbicide for maize, diketonitriles (EP 496 630, EP 496 631), in particular 2-cyano-3-cyclopropyl-1-(2-SO$_2$CH$_3$-4-CF$_3$phenyl)propane-1,3-dione and 2-cyano-3-cyclopropyl-1-(2-SO$_2$CH$_3$-4-2,3-dichlorophenyl)propane-1,3-dione, triketones (EP 625 505, EP 625 508, U.S. Pat. No. 5,506,195), in particular sulcotrione or mesotrione, or else pyrazolinates.

One of the advantages of the herbicides, whose targets are enzymes involved in the vital metabolic pathways of plants, is their broad spectrum of activity on plants of distant phylogenetic origin. However, such herbicides also have the major drawback, when they are applied to crops in order to eliminate unwanted plants or "weeds", of also acting on the cultivated plants. This drawback can be overcome by using cultivated plants that are tolerant to the herbicides. Such plants are generally obtained by means of genetic engineering by introducing into their genome a gene encoding an enzyme for resistance to the herbicide, in such a way that they overexpress the enzyme in their tissues.

The present invention also relates to methods for making plants tolerant to herbicides. For example, an increase in the flux of the HPPD substrate HPP by overexpression of a PDH enzyme constitutes a strategy for obtaining herbicide-tolerant plants, in particular plants tolerant to HPPD-inhibiting herbicides.

DETAILED DESCRIPTION OF THE INVENTION

Figure 1:
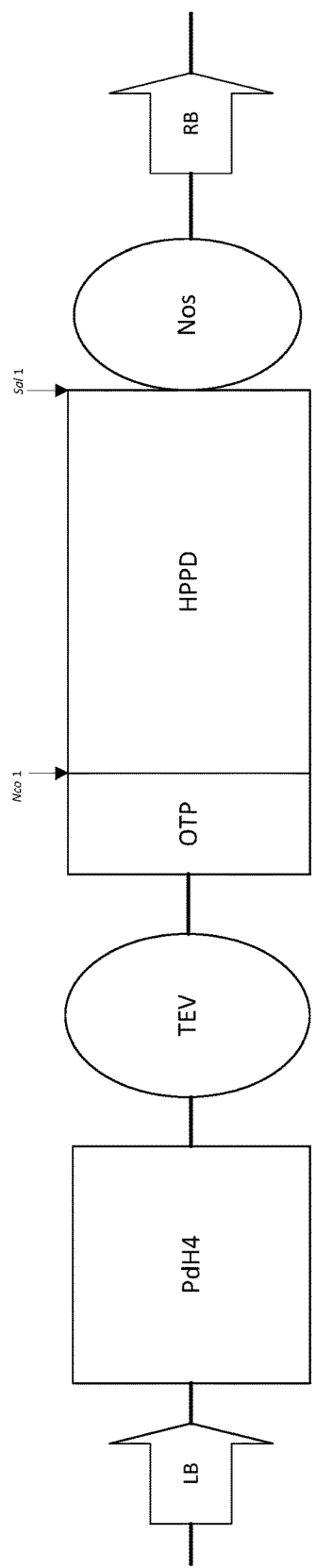
FIG. 1 shows the assembly described in Example 3.

The present invention relates to transformed plants, characterized in that they comprise: (1) a gene that is functional in plants, allowing overexpression of a PDH enzyme, (2) a gene that is functional in plants, allowing overexpression of an HPPD enzyme.

According to a particular embodiment, the invention relates to transformed plants, characterized in that they comprise: (1) a gene that is functional in plants, allowing overexpression of a PDH enzyme, (2) a gene that is functional in plants, allowing overexpression of an HPPD enzyme, with the exception of a gene that is functional in plants, allowing overexpression of a phytyl/prenyl transferase enzyme.

According to another particular embodiment, the invention relates to transformed plants, characterized in that they consist of plants transformed with: (1) a gene that is functional in plants, allowing overexpression of a PDH enzyme, and (2) a gene that is functional in plants, allowing overexpression of an HPPD enzyme.

According to a particular embodiment of the invention, the transformed plants according to the invention can be represented by transformed plant cells.

The terms "transformed plants" or "transformed plant cells" is intended to mean, according to the invention, plants or plant cells that have stably integrated into their genome at least one transgene, it being possible for the transgene to originate from the transformed plant or from any other organism. Preferably, a transgene according to the invention is represented by a chimeric gene comprising elements originating from at least one organism other than the transformed plant. In particular, a transgene according to the invention may contain, among other elements, at least one promoter, a coding sequence and a terminator originating from different organisms, the organisms also being different from the transformed plant.

In the expression "gene that is functional in plants, allowing overexpression of a PDH enzyme", the term "PDH" should be interpreted as referring to any natural or mutated PDH enzyme exhibiting the PDH activity of conversion of prephenate to HPP. In particular, the PDH enzyme can originate from any type of organism. An enzyme with PDH activity can be identified by any method that makes it possible either to measure the decrease in the amount of prephenate substrate, or to measure the accumulation of a product derived from the enzymatic reaction, i.e. HPP or one of the cofactors NADH or NADPH. In particular, the PDH activity can be measured by means of the method described in Example 2.

Many genes enclosing PDH enzymes are described in the literature. Particularly known is the gene encoding the PDH enzyme of the yeast *Saccharomyces cerevisiae* (Accession No. S46037) as described in Mannhaupt et al. (1989, Gene 85, 303-311), of a bacterium of the *Bacillus* genes, in particular of the species *B. subtilis* (Accession No. P20692) as described in Henner et al. (1986, Gene 49 (1) 147-152), of a bacterium of the *Escherichia* genus, in particular of the species *E. coli* (Accession No. KMECTD) as described in Hudson et al. (1984, J. Mol. Biol. 180(4), 1023-1051), or of a bacterium of the *Erwinia* genus, in particular of the species *E. herbicola* (Accession No. S29934) as described in Xia et al. (1992, J. Gen. Microbiol. 138(7), 1309-1316).

In the expression "gene that is functional in plants, allowing overexpression of an HPPD enzyme", the term "HPPD" should be interpreted as referring to any natural, mutated or chimeric HPPD enzyme exhibiting the HPPD activity of conversion of HPP to homogentisate. The enzymatic activity of HPPDs can be measured by any method that makes it possible either to measure the decrease in the amount of HPP substrate, or to measure the accumulation of the product derived from the enzymatic reaction, i.e. homogentisate. In particular, the HPPD activity can be measured by means of the method described in Example 1 and in Garcia et al. (1997, Biochem. J. 325, 761-769) or Garcia et al. (1999, Plant Physiol. 119, 1507-1516).

In particular, the HPPD enzyme can originate from any type of organism. Many genes encoding HPPD enzymes are described in the literature, in particular the genes of bacteria such as *Pseudomonas* (Rüetschi & al., 1992, Eur. J. Biochem., 205, 459-466, WO 96/38567), of plants such as *Arabidopsis* (WO 96/38567, Genbank AF047834) or carrot (WO 96/38567, Genbank 87257), of *Coccicoides* (Genbank COITRP), or of mammals such as mice or pigs.

According to the invention, the term "mutated HPPD" is intended to mean an HPPD having at least one mutation with respect to a natural HPPD, and having the property of being more tolerant to HPPD-inhibiting herbicides than the corresponding natural HPPD. Advantageously, the mutated HPPD is an HPPD that is mutated in its C-terminal portion, as described in patent application WO 99/24585. Preferably, the mutated HPPD comprises the mutation W336 as described in patent application WO 99/24585.

The term "chimeric HPPD" is intended to mean an HPPD comprising elements originating from various HPPDs. Such chimeric HPPDs are in particular described in patent application WO 99/24586. Advantageously, the HPPD is an HPPD from *Pseudomonas fluoescens* (WO 96/38567) or from *Arabidopsis thaliana* (WO 96/38567).

In the expression "gene that is functional in plants, allowing overexpression of a phytyl/prenyl transferase enzyme", the term "phytyl/prenyl transferase" should be interpreted as referring to a phytyl/prenyl transferase enzyme as described in patent application WO 02/089561. In particular, said "gene that is functional in plants, allowing overexpression of a phytyl/prenyl transferase enzyme" consists of a gene selected from the Synechocystis slrl 736 gene (sequence described in the Cyanobase on the website http://www.kazusa.or.jp/cyanobase), and the *Arabidopsis* ATPT2 gene (Smith et al., 1997, Plant J. 11, 83-92).

The transformed plants or plant cells according to the invention produce amounts of prenylquinones that are larger than those of non-transformed plants. Preferably, the transformed plants or plant cells according to the invention produce amounts of prenylquinones that are larger than those of plants transformed with just one of the genes that are functional in plants, allowing overexpression of a PDH or an HPPD enzyme. Preferably, the prenylquinones produced by the transformed plants or plant cells according to the invention are tocopherols and/or tocotrienols and/or plastoquinones. Many methods for measuring the amount of tocopherols, tocotrienols and plastoquinones are known and are available to those skilled in the art. By way of example, tocopherols, tocotrienols and plastoquinones can be measured by the method of Frazer et al. (2000, Plant J. 24: 551-558). According to the present invention, the term "larger amounts" is intended to mean amounts that are preferably at least twice as large, preferably at least 5 times larger, preferably at least 10 times larger, preferably at least 50 times larger, preferably at least 100 times larger, preferably at least 500 times larger, and preferably at least 1000 times larger.

The transformed plants according to the invention also have the effect of being tolerant to HPPD inhibitors.

The expression "transformed plants tolerant to HPPD inhibitors" is intended to mean transformed plants as described above exhibiting at least the characteristic of being tolerant with respect to a dose of HPPD inhibitor that is normally toxic for non-transformed identical plants. The dose of HPPD inhibitor that is normally toxic for a non-transformed plant depends on the HPPD inhibitor used and on the plant to which the inhibitor is applied, and also on the stage at which it is applied to the plant. However, those skilled in the art will be able to determine such a dose in the knowledge that the toxic nature of the inhibitor can correspond either to a lethal effect of the inhibitor resulting in death of the plant a certain number of days after application of the inhibitor, the lethal effect possibly being preceded by a "bleaching" effect on the plant, as is generally the case for HPPD inhibitors, or to an effect consisting of decreased growth of the plant. Preferably, the transformed plants tolerant to HPPD inhibitors according to the invention are tolerant with respect to a dose of HPPD inhibitor that is normally toxic for identical plants transformed with only the gene that is functional in plants, allowing overexpression of an HPPD enzyme.

The term "HPPD inhibitors" is intended to mean any compound, of natural or artificial origin, capable of binding to a plant HPPD enzyme so as to transiently or permanently block its natural enzymatic activity of conversion of HPP to homogentisate. By virtue of this property, the HPPD inhibitors according to the invention induce death or inhibition of growth of the plants to which they are applied, the death generally occurring after a "bleaching" of the plants.

By way of examples of HPPD inhibitors, mention may be made of isoxazoles (EP 418 175, EP 470 856, EP 487 352, EP 527 036, EP 560 482, EP 682 659, U.S. Pat. No. 5,424,276), in particular isoxaflutole, a selective herbicide for maize, diketonitriles (hereinafter referred to as DKNs, and described in EP 496 630, EP 496 631), in particular 2-cyano-3-cyclopropyl-1-(2-$SO_2CH_3$-4-$CF_3$ phenyl) propane-1,3-dione and 2-cyano-3-cyclopropyl-1-(2-$SO_2CH_3$-4-2,3-dichlorophenyl)propane-1,3-dione, triketones (EP 625 505, EP 625 508, U.S. Pat. No. 5,506,195), in particular sulcotrione or mesotrione, or else pyrazolinates.

According to the invention, the expression "gene that is functional in plants" is intended to mean a gene capable of functioning in a plant. A gene capable of functioning in a plant is a gene capable of expressing the protein for which it codes in at least one tissue of the plant. In particular, the genes that are functional in the plants according to the invention allow overexpression of the PDH and HPPD enzymes. The overexpression of a protein means the expression of this protein in the tissues of the transformed plant at a higher level than that existing in a non-transformed identical plant, the level being measured at an identical developmental stage of the plants. Preferably, the gene that is functional in plants according to the invention is a chimeric gene which may comprise elements originating from organisms other than the plant into which it is introduced.

The genes that are functional in plants according to the invention are preferably chimeric genes comprising at least, functionally linked to one another, a promoter that is functional in a plant, a sequence encoding a PDH enzyme and/or an HPPD enzyme, and a terminator element that is functional in this same plant. The various elements that a chimeric gene may contain are, firstly, regulatory elements for transcription, for translation and for maturation of proteins, such as a promoter, a sequence encoding a signal peptide or a transit peptide, or a terminator element constituting a polyadenylation signal, and, secondly, a sequence encoding a protein. The expression "functionally linked to one another" means that the elements of the chimeric gene are linked to one another in such a way that their function is coordinated and allows expression of the coding sequence. By way of example, a promoter is functionally linked to a coding sequence when it is capable of providing the expression of the coding sequence. The construction of a chimeric gene according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press). The choice of the regulatory elements constituting the chimeric gene depends essentially on the plant in which they must function, and those skilled in the art are capable of selecting regulatory elements that are functional in a given plant.

The promoters that the chimeric gene according to the invention may contain may be constitutive, inducible, or spatially or temporally regulated.

Among the constitutive promoters that can be used in the chimeric gene of the present invention, mention may be made, by way of example, of bacterial promoters, such as that of the octopine synthase gene or that of the nopaline synthase gene (Sanders et al., 1987, Nucleic Acids Res. 15, 1543-1548), viral promoters, such as that of the gene controlling transcription of the 19S or 35S RNA of the cauliflower mosaic virus (CaMV; Lawton et al., 1987, Plant Mol. Biol. 9, 315-324; Odell et al., 1985, Nature, 313, 810-812), or the promoters of the cassava vein mosaic virus (CsVMV; as described in patent application WO 97/48819). Among the promoters of plant origin, mention will be made of the promoter of the ribulose-biscarboxylase/oxygenase (RuBisCO) small subunit gene, the promoter of a histone gene as described in application EP 0 507 698, or the promoter of a rice actin gene (Wang et al., 1992, Mol. Cell. Biol., 12 (8): 3399-3406; U.S. Pat. No. 5,641,876).

Among the inducible promoters that can be used in the chimeric gene of the present invention, mention may be made, by way of example, of the promoter of the gene encoding the auxin-binding protein (Schwob et al., 1993, Plant J. 4 (3): 423-432), the promoter of the gene encoding UDP-glucose flavonoid glycosyltransferase (Ralston et al., 1988, Genet., 119 (1), 185-197), the promoter of the gene encoding the MIP proteinase inhibitor (Cordero et al., 1994, Plant J., 6 (2) 141-150), or the promoter of the gene encoding glyceraldehyde-3-phosphate dehydrogenase (Martinez et al., 1989, J. Mol. Biol., 208 (4), 551-565; Quigley et al., 1989, J. Mol. Evol., 29 (5), 412-421; Kohler et al., 1995, Plant Mol. Biol., 29 (6), 1293-1298).

Among the tissue-specific promoters that can be used in the chimeric gene of the present invention, mention may be made, by way of example, of root-specific promoters, such as, for example, that described in patent application WO 00/29594, flower-specific promoters, such as those described in patent applications WO 98/22593, WO 99/15679 or WO 99/43818, or fruit-specific promoters, in particular seed-specific promoters, such as those described in patent applications WO 91/13993, WO 92/17580, WO 98/45460, WO 98/45461 or WO 99/16890.

Among the terminator elements that can be used in the chimeric gene of the present invention, mention may be made, by way of example, of the nos terminator element of the gene encoding nopaline synthase from *Agrobacterium tumefaciens* (Bevan et al., 1983, Nucleic Acids Res. 11(2), 369-385), or the terminator element of a histone gene as described in application EP 0 633 317.

The chimeric gene may also comprise a subcellular targeting sequence, encoding a signal peptide or a transit peptide. Such a sequence, located upstream or downstream of the sequence encoding an HPPD enzyme or a PDH enzyme, makes it possible to direct the HPPD or PDH enzyme specifically into a cellular compartment of the host organism. For example, the chimeric gene may comprise a sequence encoding a signal peptide or a transit peptide for directing the HPPD and/or PDH enzyme to a particular compartment of the cytoplasm, such as the mitochondria, the plasts, the endoplasmic reticulum or the vacuoles.

The role of such sequences is in particular described in issue 38 of the review Plant Molecular Biology (1998) which is in large part devoted to the transport of proteins in the various compartments of the plant cell (Sorting of proteins to vacuoles in plant cells pp 127-144; the nuclear pore complex pp 145-162; protein translocation into and across the chloroplastic envelope membranes pp 91-207; multiple pathways for the targeting of thylakoid proteins in chloroplasts pp 209-221; mitochondrial protein import in plants pp 311-338).

According to one embodiment, the transit peptide may be a chloroplast targeting or mitochondrial targeting signal, which is then cleaved in the chloroplasts or the mitochondria. Preferably, the chimeric gene according to the invention comprises a subcellular targeting sequence encoding a transit peptide that targets the HPPD and/or PDH enzyme into the chloroplasts.

The transit peptides may be single or double. The double transit peptides are optionally separated by an intermediate sequence. By way of example, a preferred transit peptide according to the invention comprises, in the direction of transcription, a sequence encoding a transit peptide of a plant gene encoding an enzyme that is located in plastids, part of the sequence of the mature N-terminal portion of a plant gene encoding an enzyme that is located in plastids, and then a sequence encoding a second transit peptide of a plant gene encoding an enzyme that is located in plastids. Such double transit peptides are for example described in patent application EP 0 508 909.

According to the invention, the chimeric gene may also comprise other regulatory sequences, which are located between the promoter and the coding sequence, such as transcription activators (enhancers), for instance the transcription activator of the tobacco mosaic virus (TMV) described in application WO 87/07644, of the tobacco etch virus (TEV) described by Carrington & Freed (1990, J. Virol. 64(4):1590-7) or of the figwort mosaic virus (Figwort Mosaic Virus, U.S. Pat. No. 5,994,521). The chimeric gene according to the invention may also contain introns, in particular introns that promote the expression of genes in monocotyledonous plants, such as intron 1 of the rice actin gene described in patent application WO 99/34005, or the maize intron adh1.

The plants and the plant cells according to the invention are transformed plants and plant cells. To obtain the transformed plants and plant cells according to the invention, those skilled in the art can use one of the many known methods of transforming plants.

Preferably, the plants and the plant cells according to the invention are transformed with a cloning, expression and/or transformation vector comprising a gene that is functional in plants according to the invention, allowing overexpression of HPPD or of PDH.

The vectors that may be useful for implementing the invention are, for example, plasmids, cosmids, bacteriophages or viruses. Preferably, the vectors for transforming the plant cells or the plants according to the invention are plasmids. In general, the main qualities of a vector should be an ability to maintain itself and to self-replicate in plant cells, in particular by virtue of the presence of an origin of replication. With the aim of obtaining stable transformation of a host organism, the vector may also integrate into the genome. The choice of such a vector and also the techniques for inserting the gene according to the invention into the vector are widely described in Sambrook et al. (1989, Molecular Cloning: A Laboratory Manual, Nolan C. ed., New York: Cold Spring Harbor Laboratory Press) and are part of the general knowledge of those skilled in the art. Advantageously, the vector used in the present invention also contains, in addition to the gene according to the invention, another gene encoding a selection marker. The selection marker makes it possible to select the host organisms that are effectively transformed, i.e. those that have incorporated the vector. Among the selection markers that can be used, mention may be made of markers containing genes for resistance to antibiotics, such as, for example, that of the hygromycin phosphotransferase gene (Gritz et al., 1983, Gene 25: 179-188), but also markers containing herbicidal tolerance genes, such as the bar gene (White et al., 1990, Nucleic Acid Res. 18(4):1062) for tolerance to bialaphos, the EPSPS gene (U.S. Pat. No. 5,188,642) for tolerance to glyphosate or alternatively the HPPD gene (WO 96/38567) for tolerance to isoxazoles. Mention may also be made of genes encoding readily identifiable enzymes such as the GUS enzyme, or genes encoding pigments or enzymes that regulate the production of pigments in the transformed cells. Such selection marker genes are in particular described in patent applications WO 91/02071, WO 95/06128, WO 96/38567 and WO 97/04103.

Among the transformation methods that can be used to obtain transformed plants according to the invention, one of these consists in placing the cells or tissues of the plants to be transformed in the presence of polyethylene glycol (PEG) and of the vectors described above (Chang and Cohen, 1979, Mol. Gen. Genet. 168(1), 111-115; Mercenier and Chassy, 1988, Biochimie 70(4), 503-517). Electroporation is another method, which consists in subjecting the cells or tissues to be transformed and the vectors to an electric field (Andreason and Evans, 1988, Biotechniques 6(7), 650-660; Shigekawa and Dower, 1989, Aust. J. Biotechnol. 3(1), 56-62). Another method consists in injecting the vectors directly into the cells or the tissues by microinjection (Gordon and Ruddle, 1985, Gene 33(2), 121-136). Advantageously, the "biolistic" method may be used. It consists in bombarding cells or tissues with particles onto which the vectors are adsorbed (Bruce et al., 1989, Proc. Natl. Acad. Sci. USA 86(24), 9692-9696; Klein et al., 1992, Biotechnology 10(3), 286-291; U.S. Pat. No. 4,945,050). Preferably, the transformation of plant cells or tissues can be carried out using bacteria of the *Agrobacterium* genus, preferably by infection of the cells or tissues of the plants with *A. tumefaciens* (Knopf, 1979, Subcell. Biochem. 6, 143-173; Shaw et al., 1983, Gene 23(3):315-330) or *A. rhizogenes* (Bevan and Chilton, 1982, Annu. Rev. Genet. 16:357-384; Tepfer and Casse-Delbart, 1987, Microbiol. Sci. 4(1), 24-28). Preferably, the transformation of plant cells or tissues with *Agrobacterium tumefaciens* is carried out according to the protocol described by Ishida et al. (1996, Nat. Biotechnol. 14(6), 745-750). Those skilled in the art will choose the appropriate method according to the nature of the plant to be transformed.

A subject of the present invention is also a method for producing plants according to the invention. This method consists in regenerating transformed plants from transformed plant cells as described above. The regeneration is obtained by any appropriate method, which depends on the nature of the plant.

The invention also comprises parts of these transformed plants, and the progeny of these plants. The term "part of these plants" is intended to mean any organ of these plants, whether above ground or below ground. The organs above ground are the stems, the leaves and the flowers comprising the male and female reproductive organs. The organs below ground are mainly the roots, but they can also be tubers. The term "progeny" is intended to mean mainly the seeds containing the embryos derived from the reproduction of these plants with one another. By extension, the term "progeny" applies to all the seeds formed at each new generation derived from crosses in which at least one of the parents is a transformed plant according to the invention. Progeny can also be obtained by vegetative multiplication of the transformed plants. The seeds according to the invention can be coated with an agrochemical composition comprising at least one active product having an activity selected from fungicidal, herbicidal, insecticidal, nematicidal, bactericidal or virucidal activities.

The transformed plants according to the invention may comprise at least one other gene encoding a protein of interest, which other gene is also introduced artificially into the genome of the plant, at the same time as, before or after the gene that is functional in plants, allowing overexpression of PDH and/or HPPD. Among the genes encoding a protein of interest, mention may be made of genes encoding another enzyme for resistance to a herbicide, for example the gene encoding the bar enzyme (White et al., NAR 18:1062, 1990) for tolerance to bialaphos, or the gene encoding the EPSPS enzyme (U.S. Pat. No. 5,188,642; WO 97/04103) for tolerance to glyphosate. Mention may also be made of a gene encoding an insecticidal toxin, for example a gene encoding a δ-endotoxin of the *Bacillus thuringiensis* bacterium (for example, see International Patent Application WO 98/40490). Other genes for resistance to diseases may also be contained in these plants, for example a gene encoding the oxalate oxidase enzyme as described in patent application EP 0 531 498 or U.S. Pat. No. 5,866,778, as may a gene encoding another antibacterial and/or antifungal peptide, such as those described in patent applications WO 97/30082, WO 99/24594, WO 99/02717, WO 99/53053 and WO 99/91089. Mention may also be made of genes encoding agronomic characteristics of the plant, in particular a gene encoding a delta-6 desaturase enzyme as described in U.S. Pat. No. 5,552,306, U.S. Pat. No. 5,614,313, and patent applications WO 98/46763 and WO 98/46764, or a gene encoding a serine acetyltransferase (SAT) enzyme as described in patent applications WO 00/01833 and WO 00/36127.

The additional genes encoding a protein of interest can be integrated by means of a vector. In this case, the vector comprises a gene according to the invention encoding a PDH enzyme and/or an HPPD enzyme, and at least one gene encoding another peptide or protein of interest.

They can also be integrated by means of at least one other vector comprising the additional gene, according to the usual techniques defined above.

The plants according to the invention can also be obtained by crossing of plants, one carrying the gene encoding a PDH enzyme and/or an HPPD enzyme according to the invention, the other carrying another gene encoding at least one other peptide or protein of interest.

The transformed plants according to the invention may be monocotyledons or dicotyledons. Preferably, these plants are plants of agronomic interest. Advantageously, the monocotyledonous plants are wheat, maize or rice. Advantageously, the dicotyledonous plants are rapeseed, soybean, tobacco or cotton.

The present invention also relates to a method for cultivating the transformed plants according to the invention, characterized in that it consists in planting the seeds of the transformed plants over an area of a field that is suitable for the cultivation of the plants, in applying to the area of the field at least one herbicidal composition comprising an HPPD inhibitor, without substantially affecting the seeds or the transformed plants, and then in harvesting the cultivated plants when they reach the desired maturity and, optionally, in separating the seeds from the harvested plants.

The present invention also relates to a method for conferring on plants a tolerance to HPPD inhibitors, characterized in that the plants are transformed, simultaneously or successively, with: (1) a gene that is functional in plants, allowing overexpression of a PDH enzyme, (2) a gene that is functional in plants, allowing overexpression of an HPPD enzyme.

The present invention also relates to use of the plants or plant cells according to the invention, for producing prenylquinones, in particular tocopherols, tocotrienols and/or plastoquinones.

The present invention also relates to a method for increasing the amount of prenylquinones in plants, characterized in that the plants are transformed, simultaneously or successively, with: (1) a gene that is functional in plants, allowing overexpression of a PDH enzyme, (2) a gene that is functional in plants, allowing overexpression of an HPPD enzyme.

The present invention also relates to a method for producing prenylquinones, characterized in that it comprises a step of cultivating a transformed plant cell or plant according to the invention in a cultivation medium suitable for the growth and for the multiplication of the plant cell or of the plant.

According to a particular embodiment of the method, the prenylquinones produced are preferably tocopherols represented by vitamin E.

According to particular embodiment of the method, the prenylquinones produced are preferably tocotrienols.

According to a particular embodiment of the invention, the method for producing prenylquinones comprises a subsequent step of extraction of the prenylquinones produced by the transformed plant cell or by the transformed plant cultivated in the first step.

When the method for producing prenylquinones is carried out with transformed plant cells according to the invention, the plant cells are cultivated in a cultivation medium that promotes their survival and their growth. Those skilled in the art will be able to determine the composition of the cultivation medium so as to allow optimal growth of the plant cells. By way of examples, methods and media for cultivating plant cells are described in Murashige and Skoog (1962, Physiol. Plant. 15: 473-497) and in Gamborg et al. (1968, Exptl. Cell Research, 50:151-159).

In addition, when the method is carried out with transformed plant cells according to the invention, the prenylquinones produced may or may not be secreted into the cultivation medium. When the prenylquinones are secreted into the cultivation medium, the extraction step of the method may be preceded by a step in which the cultivation medium is recovered by elimination of the plant cells. Such a step in which the cultivation medium is recovered by elimination of the plant cells can be carried out by any means of separating solid fractions included in a liquid fraction. In particular, filtration and centrifugation are suitable means for carrying out this step.

When the prenylquinones are not secreted into the cultivation medium, the extraction step can be carried out by the succession of steps consisting in concentrating the cultivated plant cells, in rupturing the isolated plant cells, in centrifuging the ruptured cell extract, and then in recovering the supernatant comprising the prenylquinones. The cell rupturing step can be carried out using techniques known to those skilled in the art such as mechanical grinding (by pressure difference, by the action of ultrasound, by trituration), enzymatic lysis or osmotic shock, it being possible for the techniques to be used individually or in combination.

When the method for producing prenylquinones is carried out with transformed plants according to the invention, the plants are cultivated on a substrate that is suitable for their survival and for their growth, it being possible for the substrate to be natural or artificial. A natural substrate may, for example, be soil, or a mixture of soils, and the plants may be cultivated under controlled conditions such as, for example, in a cultivation chamber, under semi-controlled conditions such as, for example, in a greenhouse, or under natural conditions such as, for example, in an open field. An artificial substrate may, for example, be a liquid substrate or an agar substrate, the composition of which promotes the survival and the growth of the plants according to the invention. Those skilled in the art will be able to determine the composition of the artificial substrate in such a way as to allow optimal growth of the plants. By way of example of substrates for cultivating plants, mention may be made of media such as rock wool or vermiculite, irrigated with a nutritive solution containing the nutritive elements N (nitrogen), P (phosphorus) and K (potassium), or any other commercial or adapted nutritive solution that allows plants to grow on these media. When the plants according to the invention are cultivated on an artificial substrate, they are generally cultivated under controlled conditions in a cultivation chamber.

In addition, when the method is carried out with transformed plants according to the invention, the prenylquinones produced are generally immobilized in the transformed plants.

The transformed plants according to the invention, or a part of the plants, can either be used directly and incorporated into food compositions intended for the human or animal diet, or can undergo extraction of the prenylquinones that they contain. As indicated above, the term "part of plants" is intended to mean any organ of these plants, whether above ground or below ground. The organs above ground are the stems, the leaves and the flowers comprising the male and female reproductive organs, and also the seeds. The organs below ground are mainly the roots, but they can also be tubers. According to a preferred embodiment of the invention, the seeds are the parts of the transformed plants that are intended for food.

The invention also comprises the seeds of the transformed plants according to the invention, the seeds being rich in prenylquinones compared with seeds of non-transformed plants. In addition, the invention also comprises food compositions comprising seeds or any other part of the transformed plants according to the invention. The oil produced from these parts of plants, in particular from the seeds, is also a subject of the present invention.

In order to recover the prenylquinones produced in the transformed plant, an extraction step can be carried out by means of the succession of steps consisting in grinding the cultivated plants, in filtering and/or centrifuging the ground plant material, and then in recovering the supernatant comprising the prenylquinones, it being possible for the recovery to consist of an extraction of the lipid compounds. Preferably, the grinding step consists of mechanical grinding (by pressure difference, by the action of ultrasound, by trituration), which may be followed by enzymatic lysis or by osmotic shock.

The present method can also implement a final step of purification of the prenylquinones contained in the extract of plant cell or of plant obtained. The purification of the prenylquinones can be carried out by any technique for concentrating or for separating compounds, in particular the techniques of microfiltration, ultrafiltration, electrophoresis or chromatography that are well known to those skilled in the art. In order to achieve purified prenylquinones, those skilled in the art will be able to use a method for measuring the prenylquinones in order to identify the purification fraction(s) containing the prenylquinones. According to this method, the prenylquinones produced can have a purity of preferably 50%, 60%, 70%, 80%, 90%, 95%, 99% or advantageously 100%.

According to a particular embodiment of the invention, the transformed plants according to the invention comprise, in addition to a gene that is functional in plants, allowing overexpression of a PDH enzyme and a gene that is functional in plants, allowing overexpression of an HPPD enzyme, a gene that is functional in plants, allowing overexpression of a geranyl-geranyl reductase enzyme (hereinafter referred to as GGR). Among the prenylquinones produced, such plants preferentially produce tocopherols, in particular vitamin E, as compared to tocotrienols and to plastoquinones.

The GGR enzyme is an enzyme that catalyzes the conversion of geranyl-geranyl pyrophosphate to phytylpyrophosphate. According to a particular embodiment, the gene that is functional in plants, allowing overexpression of GGR, comprises the coding sequence of a gene encoding a plant GGR. By way of example, use may be made of the sequence encoding the GGR of *Arabidopsis*, as published in Keller et al., (1998, Eur. J. Biochem. 251(1-2): 413-417), or those described by accession numbers AJ 007789 (tobacco), AF 069318 (*Mesembryanthenum crystallinum*), Y14004 (*Arabidopsis*), and Q55087 (*Synechocystis* sp PCC 6803).

BIBLIOGRAPHICAL REFERENCES

Abou-Zeid et al., 1995, Applied Env Microb. 41:1298-1302.
Andreason G L, Evans G A. Introduction and expression of DNA molecules in eukaryotic cells by electroporation. Biotechniques. 1988 July-August; 6(7):650-60.
Ausubel et al., 1994, Current Protocols in Molecular Biology, Current Protocols, USA, Vol. 1-2.
Bevan M, Barnes W M, Chilton M D. Structure and transcription of the nopaline synthase gene region of T-DNA. Nucleic Acids Res. 1983 Jan. 25; 11(2):369-85.
Bevan M W, Chilton M D. T-DNA of the *Agrobacterium* Ti and Ri plasmids. Annu Rev Genet. 1982; 16:357-84. Review.
Bonner et al., 1995, Plant Cells Physiol. 36:1013-1022.
Brown, 1998, Molecular Biology LabFax, Second edition, Academic Press, UK
Bruce W B, Christensen A H, Klein T, Fromm M, Quail P H. Photoregulation of a phytochrome gene promoter from oat transferred into rice by particle bombardment. Proc Natl Acad Sci USA. 1989 December; 86(24):9692-6.
Byng et al., 1981, Phytochemistry. 6:1289-1292.
Carrington J C, Freed D D. Cap-independent enhancement of translation by a plant potyvirus 5' nontranslated region. J Virol. 1990 April; 64(4):1590-7.
Chang S, Cohen S N. High frequency transformation of *Bacillus subtilis* protoplasts by plasmid DNA. Mol Gen Genet. 1979 Jan. 5; 168(1):111-5.
Connely and Conn, 1986, Z. Naturforsch. 41c:69-78.
Cordero M J, Raventos D, San Segundo B. Expression of a maize proteinase inhibitor gene is induced in response to wounding and fungal infection: systemic wound-response of a monocot gene. Plant J. 1994 August; 6(2):141-50.
Croy R. D. D., 1993, Plant Molecular Biology LabFax, BIOS Scientific Publications Ltd (UK) and Blackwell Scientific Publications (UK)
Dieffenbach and Dvekaler, 1995, PCR Primer: A laboratory manual, Cold Spring Harbor Laboratory Press, NY
Ellis M K, Whitfield A C, Gowans L A, Auton T R, Provan W M, Lock E A, Lee D L, Smith L L. Characterization of the interaction of 2-[2-nitro-4-(trifluoromethyl)benzoyl]-4,4,6,6,-tetramethyl-cyclohexane-1,3,5-trione with rat hepatic 4-hydroxyphenylpyruvate dioxygenase. Chem Res Toxicol. 1996 January-February; 9(1):24-27.
Epstein S S, Forsyth J, Saporoschetz I B, Mantel N. An exploratory investigation on the inhibition of selected photosensitizers by agents of varying antioxidant activity. Radiat Res. 1966 June; 28(2):322-35.
Folch J, Lees M, Sloane Stanley G H A simple method for the isolation and purification of total lipides from animal tissues. J Biol Chem. 1957 May; 226(1):497-509.
Fraser P D, Pinto M E, Holloway D E, Bramley P M. Technical advance: application of high-performance liquid chromatography with photodiode array detection to the metabolic profiling of plant isoprenoids. Plant J. 2000 November; 24(4):551-8.
Gaines et al., 1982, Planta. 156:233-240.
Gamborg O L, Miller R A, Ojima K. Nutrient requirements of suspension cultures of soybean root cells. Exp Cell Res. 1968 April; 50(1):151-8.
Garcia I, Rodgers M, Lenne C, Rolland A, Sailland A, Matringe M. Subcellular localization and purification of a p-hydroxyphenylpyruvate dioxygenase from cultured carrot cells and characterization of the corresponding cDNA. Biochem J. 1997 Aug. 1; 325 (Pt 3):761-9.
Garcia I, Rodgers M, Pepin R, Hsieh T F, Matringe M. Characterization and subcellular compartmentation of recombinant 4-hydroxyphenylpyruvate dioxygenase from *Arabidopsis* in transgenic tobacco. Plant Physiol. 1999 April; 119(4):1507-16.
Goodwin, 1972, in Tyrosine Metabolism: The biochemical, physiological, and clinical significance of p-hydroxyphenlypyruvate oxygenase, Goodwin B. L., Ed., Oxford University Press:1-94.
Gordon J W, Ruddle F H. DNA-mediated genetic transformation of mouse embryos and bone marrow—a review. Gene. 1985; 33(2):121-36.
Gritz L, Davies J. Plasmid-encoded hygromycin B resistance: the sequence of hygromycin B phosphotransferase gene and its expression in *Escherichia coli* and *Saccharomyces cerevisiae*. Gene. 1983 November; 25(2-3):179-88.
Grumbach, 1984, Structure Function and Metabolisme of plant lipids, Siegenthaler and Eichenberger eds.
Guthrie N, Gapor A, Chambers A F, Carroll K K. Inhibition of proliferation of estrogen receptor-negative MDA-MB-435 and -positive MCF-7 human breast cancer cells by palm oil tocotrienols and tamoxifen, alone and in combination. J Nutr. 1997 March; 127(3):544S-548S.
Henner D J, Band L, Flaggs G, Chen E The organization and nucleotide sequence of the *Bacillus subtilis* hisH, tyrA and aroE genes. Gene. 1986; 49(1):147-52.

Horsch et al., 1985, Science 227:1229-1231.

Hudson G S, Davidson B E. Nucleotide sequence and transcription of the phenylalanine and tyrosine operons of *Escherichia coli* K12. J Mol Biol. 1984 Dec. 25; 180(4):1023-51.

Ishida Y, Saito H, Ohta S, Hiei Y, Komari T, Kumashiro T. High efficiency transformation of maize (*Zea mays* L.) mediated by *Agrobacterium tumefaciens*. Nat Biotechnol. 1996 June; 14(6):745-50.

Kamat J P, Sarma H D, Devasagayam T P, Nesaretnam K, Basiron Y. Tocotrienols from palm oil as effective inhibitors of protein oxidation and lipid peroxidation in rat liver microsomes. Mol Cell Biochem. 1997 May; 170(1-2):131-7.

Kamal-Eldin A, Appelqvist L A. The chemistry and antioxidant properties of tocopherols and tocotrienols. Lipids. 1996 July; 31(7):671-701.

Keller Y, Bouvier F, d'Harlingue A, Camara B. Metabolic compartmentation of plastid prenyllipid biosynthesis—evidence for the involvement of a multifunctional geranylgeranyl reductase. Eur J Biochem. 1998 Jan. 15; 251(1-2):413-7.

Klein T M, Arentzen R, Lewis P A, Fitzpatrick-McElligott S. Transformation of microbes, plants and animals by particle bombardment. Biotechnology (N Y). 1992 March; 10(3):286-91. Review.

Knopf U C. Crown-gall and *Agrobacterium tumefaciens*: survey of a plant-cell-transformation system of interest to medicine and agriculture. Subcell Biochem. 1979; 6:143-73.

Kohler U, Liaud M F, Mendel R R, Cerff R, Hehl R. The maize GapC4 promoter confers anaerobic reporter gene expression and shows homology to the maize anthocyanin regulatory locus C1. Plant Mol Biol. 1995 December; 29(6):1293-8.

Lawton et al., Plant Mol. Biol. 9, 315-324

Lingens F, Goebel W, Uesseler H. [Regulation of the biosynthesis of aromatic amino acids in *Saccharomyces cerevisiae*. 2. Repression, induction and activation] Eur J Biochem. 1967 May; 1(3):363-74.

Mannhaupt G, Stucka R, Pilz U, Schwarzlose C, Feldmann H. Characterization of the prephenate dehydrogenase-encoding gene, TYR1, from *Saccharomyces cerevisiae*. Gene. 1989 Dec. 28; 85(2):303-11.

Martinez P, Martin W, Cerff R. Structure, evolution and anaerobic regulation of a nuclear gene encoding cytosolic glyceraldehyde-3-phosphate dehydrogenase from maize. J Mol Biol. 1989 Aug. 20; 208(4):551-65.

McPherson et al., 2000, PCR—Basics: From background to bench, First edition, Springer Verlag, Germany Mercenier A, Chassy B M. Strategies for the development of bacterial transformation systems. Biochimie. 1988 April; 70(4):503-17.

Murashige and Skoog, 1962, Physiol. Plant. 15:473-497.

Odell J T, Nagy F, Chua N H. Identification of DNA sequences required for activity of the cauliflower mosaic virus 35S promoter. Nature. 1985 Feb. 28-Mar. 6; 313 (6005):810-2.

Packer L, Weber S U, Rimbach G. Molecular aspects of alpha-tocotrienol antioxidant action and cell signalling. J Nutr. 2001 February; 131(2):369S-73S.

Padgette S R, Re D B, Gasser C S, Eichholtz D A, Frazier R B, Hironaka C M, Levine E B, Shah D M, Fraley R T, Kishore G M. Site-directed mutagenesis of a conserved region of the 5-enolpyruvylshikimate-3-phosphate synthase active site. J Biol Chem. 1991 Nov. 25; 266(33):22364-9.

Pearce B C, Parker R A, Deason M E, Qureshi A A, Wright J J. Hypocholesterolemic activity of synthetic and natural tocotrienols. J Med Chem. 1992 Oct. 2; 35(20):3595-606.

Quigley F, Brinkmann H, Martin W F, Cerff R. Strong functional GC pressure in a light-regulated maize gene encoding subunit GAPA of chloroplast glyceraldehyde-3-phosphate dehydrogenase: implications for the evolution of GAPA pseudogenes. J Mol Evol. 1989 November; 29(5):412-21.

Qureshi A A, Salser W A, Parmar R, Emeson E E. Novel tocotrienols of rice bran inhibit atherosclerotic lesions in C57BL/6 ApoE-deficient mice. J Nutr. 2001 October; 131(10):2606-18.

Ralston E J, English J J, Dooner H K. Sequence of three bronze alleles of maize and correlation with the genetic fine structure. Genetics. 1988 May; 119(1):185-97.

Ruetschi U, Odelhog B, Lindstedt S, Barros-Soderling J, Persson B, Jornvall H. Characterization of 4-hydroxyphenylpyruvate dioxygenase. Primary structure of the *Pseudomonas* enzyme. Eur J Biochem. 1992 Apr. 15; 205(2):459-66.

Sambrook et al., 1989, Molecular Cloning: A Laboratory Manual, Second edition, Nolan C., ed, Cold Spring Harbor Laboratory Press, NY Sambrook and Russell, 2001, Molecular cloning:A laboratory manual, Third edition, Cold Spring Harbor Laboratory Press, NY Sampathkumar P, Morrison J F. Chorismate mutase-prephenate dehydrogenase from *Escherichia coli*. Purification and properties of the bifunctional enzyme. Biochim Biophys Acta. 1982 Apr. 3; 702(2):204-11.

Sanders P R, Winter J A, Bamason A R, Rogers S G, Fraley R T. Comparison of cauliflower mosaic virus 35S and nopaline synthase promoters in transgenic plants. Nucleic Acids Res. 1987 Feb. 25; 15(4):1543-58.

Schwob E, Choi S Y, Simmons C, Migliaccio F, Ilag L, Hesse T, Palme K, Soll D. Molecular analysis of three maize 22 kDa auxin-binding protein genes—transient promoter expression and regulatory regions. Plant J. 1993 September; 4(3):423-32.

Shaw C H, Leemans J, Shaw C H, van Montagu M, Schell J. A general method for the transfer of cloned genes to plant cells. Gene. 1983 September; 23(3):315-30.

Shigekawa K, Dower W J. Electroporation: a general approach to the introduction of macromolecules into prokaryotic and eukaryotic cells. Aust J Biotechnol. 1989 January; 3(1):56-62.

Tepfer M, Casse-Delbart F. *Agrobacterium* rhizogenes as a vector for transforming higher plants. Microbiol Sci. 1987 January; 4(1):24-8.

Viviani et al., 1998, Pestic. Biochem. Physiol. 62: 125-134.

Wang Y, Zhang W, Cao J, McElroy D, Wu R. Characterization of cis-acting elements regulating transcription from the promoter of a constitutively active rice actin gene. Mol Cell Biol. 1992 August; 12(8):3399-406.

White et al., 1990, Nucleic Acid Res. 18(4):1062

Xia T, Zhao G, Fischer R S, Jensen R A. A monofunctional prephenate dehydrogenase created by cleavage of the 5' 109 bp of the tyrA gene from *Erwinia herbicola*. J Gen Microbiol. 1992 July; 138(7):1309-16.

| | | |
|---|---|---|
| WO 87/07644 | WO 95/06128 | WO 97/48819 |
| WO 91/02071 | WO 96/38567 | WO 98/22593 |
| WO91/13993 | WO 97/04103 | WO 98/40490 |
| WO 92/17580 | WO 97/30082 | WO 98/45460 |
| WO 98/45461 | WO 00/29594 | EP 0 633 317 |

-continued

| | | |
|---|---|---|
| WO 98/46763 | WO 00/36127 | EP 0 242 236 |
| WO 98/46764 | U.S. Pat. No. 4,945,050 | EP 0 293 356 |
| WO 99/02717 | U.S. Pat. No. 5,424,276 | EP 0 337 899 |
| WO 99/15679 | U.S. Pat. No. 5,994,521 | EP 0 418 175 |
| WO 99/16890 | U.S. Pat. No. 5,188,642 | EP 0 470 856 |
| WO 99/24585 | U.S. Pat. No. 5,506,195 | EP 0 487 352 |
| WO 99/24586 | U.S. Pat. No. 5,552,306 | EP 0 496 630 |
| WO 99/24594 | U.S. Pat. No. 5,614,313 | EP 0 496 631 |
| WO 99/34005 | U.S. Pat. No. 5,866,778 | EP 0 527 036 |
| WO 99/43818 | U.S. Pat. No. 5,641,876 | EP 0 560 482 |
| WO 99/53053 | EP 0 507 698 | EP 0 625 505 |
| WO 99/91089 | EP 0 508 909 | EP 0 625 508 |
| WO 00/01833 | EP 0 531 498 | EP 0 682 659 |

The examples below make it possible to illustrate the invention without, however, limiting the scope thereof.

EXAMPLES

All the methods or processes described below in these examples are given by way of examples and correspond to a choice, made among the various methods available for achieving the same result. This choice has no effect on the quality of the result and, consequently, any suitable method can be used by those skilled in the art in order to achieve the same result. In particular, and unless otherwise specified in the examples, all the recombinant DNA techniques used are carried out according to the standard protocols described in Sambrook et al. (1989, Molecular Cloning: A Laboratory Manual, Second edition, Nolan C. ed., Cold Spring Harbor Laboratory Press, NY), in Sambrook and Russel (2001, Molecular cloning: A Laboratory Manual, Third edition, Cold Spring Harbor Laboratory Press, NY), in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in R. D. D. Croy (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR—Basics: From background to bench, First edition, Springer Verlag, Germany).

Example 1: Measurement of HPPD Activity

The HPPD activity can be measured by the method described in Garcia et al. (1997, Biochem. J. 325, 761-769) or Garcia et al. (1999, Plant Physiol. 119, 1507-1516).

Example 2: Measurement of Prephenate Dehydrogenase Activity

The prephenate dehydrogenase activity is measured at 25° C. by spectrophotometric monitoring at 340 nm of the formation of NADH or NADPH in a solution containing 50 mM of tris-HCl, pH 8.6, 300 µM of prephenate, and 1 mM of NAD or NADP in a total volume of 200 µl.

Example 3: Construction of a Chimeric Gene Overexpressing HPPD

A chimeric gene allowing overexpression of HPPD for conferring on plants resistance to HPPD-inhibiting herbicides was constructed.

It consists in assembling, in the direction of transcription, a "double histone" promoter (PdH4) as described in patent application EP 0 507 698, the tobacco etch virus translational enhancer (TEV) sequence described in Carrington and Freed (1990; J. Virol. 64: 1590-1597), a sequence encoding an optimized transit peptide (OTP) as described in patent application EP 0 508 909, the coding portion of the *Arabidopsis thaliana* HPPD gene described in patent application WO 96/38567, and then the nos terminator of the nopaline synthase gene described in Bevan et al. (1983, Nucleic Acids Res. 11(2), 369-385). The assembly is then cloned into a binary vector and has the structure shown in FIG. 1:

Example 4: Construction of a Chimeric Gene Overexpressing PDH

Figure 2:
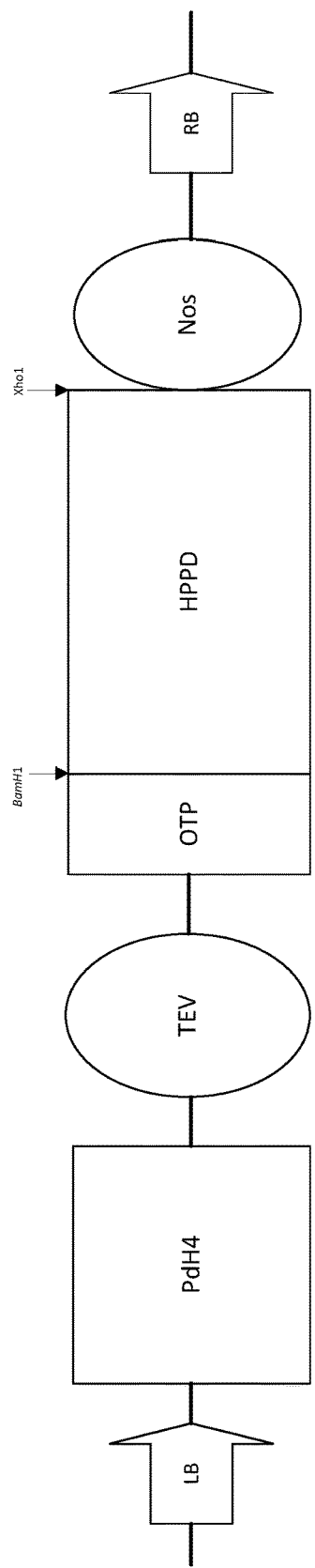
FIG. 2 shows the assembly described in Example 4.

The construction of a chimeric gene overexpressing PDH consists in assembling, in the direction of transcription, a "double histone" promoter (PdH4) as described in patent application EP 0 507 698, the tobacco etch virus translational enhancer (TEV) sequence described in Carrington and Freed (1990; J. Virol. 64: 1590-1597), a sequence encoding an optimized transit peptide (OTP) as described in patent application EP 0 508 909, the coding portion of the yeast PDH gene described in Mannhaupt et al. (1989, Gene 85, 303-311) and the nos terminator of the nopaline synthase gene described in Bevan et al. (1983, Nucleic Acids Res. 11(2), 369-385). The assembly was then cloned into the binary vector pRD 224 containing a kanamycin resistance gene (NPTII), to give the vector pRD 224-PDH. This vector has the structure shown in FIG. 2:

This binary vector was then used to transform the *Agrobacterium* strain EHA 105 and to give the *Agrobacterium* strain EHA 105-pRD 224-PDH. This *Agrobacterium* strain was used to transform tobacco PBD6 and tobacco PBD6-ARA9 (tobacco transformed with the chimeric gene allowing overexpression of the *Arabidopsis thaliana* HPPD.

The transformed plants are selected on kanamycin.

Example 5: Transformation of Tobacco PBD6-ARA9 with an Expression Cassette Overexpressing PDH The PBD6-ARA9 tobacco plants are tobacco plants transformed with a chimeric gene as described in Example 3, and overexpressing the *A. thaliana* HPPD described in patent application WO 96/38567. The method for obtaining the PBD6-ARA9 tobacco plants is described in Garcia et al. (1999, Plant Physiol. 119, 1507-1516). The PBD6-ARA9 lines transformed with the chimeric gene overexpressing PDH as described in Example 4 are called ARA9-PDH lines.
5.1: Transformation
The transformation is carried out with the nononcogenic *Agrobacterium tumefaciens* strain EHA 105-pRD 224-PDH according to the foliar disk technique (Horsch et al., 1985, Science 227: 1229-1231).
5.2: Regeneration
The regeneration of the ARA9-PDH tobacco plant is carried out from foliar explants on a Murashige and Skoog (MS) basic medium comprising 30 g/l of sucrose and also 350 mg/l of cefotaxime and 200 mg/ml of kanamycin. The foliar explants are taken from plants in a greenhouse and regenerated according to the foliar disk technique (Horsch et al., 1985, Science 227:1229-1231) in three successive steps:
The first comprises induction of the shoots on an MS medium supplemented with 30 g/l of sucrose containing 0.05 mg/l of naphthylacetic acid (ANA) and 2 mg/l of benzylaminopurine (BAP) for 15 days and 200 mg/ml of kanamycin.

The green shoots formed during this step are then developed by cultivating on an MS medium supplemented with 30 g/l of sucrose and 200 mg/ml of kanamycin, but containing no hormone, for 10 days.

Developed shoots are subsequently removed, and then cultivated on an MS rooting medium with half the content of salts, vitamins and sugars, with 200 mg/ml of kanamycin, and with no hormone. After approximately 15 days, the rooted shoots are transferred into a greenhouse.

The tolerance of the transformed plants is studied by sowing on a soil treated with diketonitrile (DKN).

Example 6: Tolerance of the PBD6-ARA9 and ARA9-PDH Tobacco Plants to HPPD Inhibitors 6.1. Tolerance to Diketonitrile (DKN)

13 ARA9-PDH lines and the PBD6-ARA9 line that was used as starting material for the transformation were sown on increasing concentrations of DKN:5, 10 and 32 ppm.

At 5 ppm of DKN, all the PBD6-ARA9 and ARA9-PDH lines are resistant, in particular since they all overexpress the *A. thaliana* HPPD. At 10 ppm of DKN, the parental line PBD6-ARA9 is completely inhibited. On the other hand, all the ARA9-PDH lines resist well, with the exception of just one (ARA9-PDH4) which is inhibited. At 32 ppm of DKN, all the ARA9-PDH lines that were resistant to 10 ppm of DKN have plants that are resistant and grow normally, whereas the parent line PBD6-ARA9 that expresses only the recombinant HPPD is completely inhibited. The lines that show the best tolerance are the ARA9-PDH14, ARA9-PDH 18 and ARA9-PDH24 lines.

6.2. Tolerance to Sulcotrione and to Mesotrione

The same experiment was carried out with the HPPD inhibitors sulcotrione and mesotrione. The ARA9-PDH18 line was found to be tolerant to 3 µM of mesotrione and to 6 µM of sulcotrione, whereas a wild-type tobacco line of the Petit Havana type is sensitive to 0.375 µM of these two compounds.

Example 7: Measurement of the Tocopherol and Tocotrienol Levels in PBD6-ARA9 and ARA9-PDH Tobacco Plants A lipid extract is obtained by the method of Folch (Folch et al., 1957, J. Biol. Chem., 226-497) from samples of medium leaves and of very young leaves of each of the plants analyzed. An analysis of their tocopherol and tocotrienol contents is then carried out by HPLC according to the method of Frazer et al. (2000, Plant J. 24:551-558). These contents are then quantified with respect to reference products, and then expressed in µg per g of solids. The results are given in Table 1.

TABLE 1

Tocopherol and tocotrienol levels in samples from the PBD6, PBD6-ARA9 (ARA9) and ARA9-PDH (PDH4, PDH 14, PDH 18, PDH 24) plants.

| | PBD6 | ARA9 | PDH 4 | PDH 14 | PDH 18 | PDH 24 |
|---|---|---|---|---|---|---|
| | (µg per g of solids) | | | | | |
| Medium leaves | | | | | | |
| α tocopherol | 62.2 | 64.73 | 66.9 | 89.7 | 91.03 | 83.4 |
| β/γ tocopherol | 1.73 | 1.93 | 2.16 | 4.56 | 4.28 | 4.01 |

TABLE 1-continued

Tocopherol and tocotrienol levels in samples from the PBD6, PBD6-ARA9 (ARA9) and ARA9-PDH (PDH4, PDH 14, PDH 18, PDH 24) plants.

| | PBD6 | ARA9 | PDH 4 | PDH 14 | PDH 18 | PDH 24 |
|---|---|---|---|---|---|---|
| | (µg per g of solids) | | | | | |
| δ tocopherol | nd | nd | nd | nd | nd | nd |
| α tocotrienol | nd | nd | nd | 64.58 | 66.99 | 55.35 |
| β/γ tocotrienol | nd | nd | nd | 2.04 | 2.23 | 1.98 |
| δ tocotrienol | nd | nd | nd | nd | nd | nd |
| Very young leaves | | | | | | |
| α tocopherol | 73.5 | 64.73 | 68.7 | 76.2 | 75.4 | 83.4 |
| β/γ tocopherol | 1.83 | 2.37 | 1.86 | 3.32 | 3 | 3.5 |
| δ tocopherol | nd | nd | nd | nd | nd | nd |
| α tocotrienol | nd | nd | nd | 275.26 | 224.5 | 242.4 |
| β/γ tocotrienol | nd | nd | nd | 17.45 | 15.3 | 17.14 |
| δ tocotrienol | nd | nd | nd | 6.2 | 4.3 | 5.4 |

These results clearly show that the ARA9-PDH tobacco plants doubly transformed with chimeric genes allowing overexpression of the PDH and HPPD enzymes have larger amounts of prenylquinones, in particular of tocopherols and of tocotrienols, compared with the PBD6-ARA9 tobacco plants singly transformed with a gene encoding an HPPD enzyme. The greatest effect concerns the tocotrienols. This effect is all the more marked in the very young leaves rich in meristematic tissues. The cause of this tissue-specificity is linked to the promoter used to create the ARA9-PDH tobacco plants, which is a promoter that is expressed preferentially in the rapidly growing tissues of plants, in particular the meristems (PdH4). The use of other types of promoters should make it possible to obtain a similar effect in other tissues of the plant.

Furthermore, the differences observed between the various ARA9-PDH lines come from the fact that different transformation events are involved. Crosses between the best lines aimed at developing homozygous lines should make it possible to obtain lines that are homogeneous with regard to the production of prenylquinones and to the tolerance to HPPD inhibitors.

The foregoing merely illustrates the principles of the present invention. Various modifications and alterations to the described embodiments will be apparent to those of ordinary skill in the art in view of the teachings herein. It will thus be appreciated that those of ordinary skill in the art will be able to make and use the present invention in ways that, although not explicitly shown or described herein, embody the principles of the invention and are thus within the spirit and scope of the invention.

INCORPORATION BY REFERENCE

The contents of all publications and references cited herein are hereby incorporated herein by reference in their entireties.

We claim:

1. A method for cultivating a transformed plant, the method comprising
   a) planting a seed of the transformed plant,
   b) contacting the seed or a transformed plant grown from the seed with a herbicidal composition comprising an inhibitor of p-hydroxyphenylpyruvate dioxygenase, and c) cultivating the plant, wherein the transformed seed or the transformed plant is substantially unaffected by the herbicidal composition, wherein the plant comprises:
  (1) a first gene that is functional in a plant, wherein the first gene comprises a nucleotide sequence that encodes a yeast prephenate dehydrogenase, and
  (2) a second gene that is functional in a plant, wherein the second gene comprises a nucleotide sequence that encodes a p-hydroxyphenylpyruvate dioxygenase, and wherein the plant overexpresses the prephenate dehydrogenase and the p-hydroxyphenylpyruvate dioxygenase, and wherein said plant is tolerant to an amount of said inhibitor that is toxic to or decreases the growth of plants transformed with said second gene alone.

2. A method for increasing the tolerance of a plant to an inhibitor of a p-hydroxyphenyl-pyruvate dioxygenase, the method comprising:
  a) applying an herbicidal composition comprising an inhibitor of p-hydroxyphenyl-pyruvate dioxygenase to a plant transformed with:
    (1) a first gene that is functional in a plant, wherein the first gene comprises a nucleotide sequence that encodes a yeast prephenate dehydrogenase, and
    (2) a second gene that is functional in a plant, wherein the second gene comprises a nucleotide sequence that encodes a p-hydroxyphenylpyruvate dioxygenase, and wherein the plant overexpresses the prephenate dehydrogenase and the p-hydroxyphenylpyruvate dioxygenase, thereby increasing the tolerance of said plant to an inhibitor of a p-hydroxyphenylpyruvate dioxygenase, and wherein said plant is tolerant to an amount of said inhibitor that is toxic to or decreases the growth of plants transformed with said second gene alone and
  b) cultivating the plant.

3. The method of claim 1, wherein said p-hydroxyphenylpyruvate dioxygenase is a plant p-hydroxyphenylpyruvate dioxygenase.

4. The method of claim 2, wherein said p-hydroxyphenylpyruvate dioxygenase is a plant p-hydroxyphenylpyruvate dioxygenase.

5. A method for cultivating a transformed plant, the method comprising
  a) planting a seed of the transformed plant,
  b) contacting the seed or a transformed plant grown from the seed with a herbicidal composition comprising an inhibitor of p-hydroxyphenylpyruvate dioxygenase, and
  c) cultivating the plant, wherein the transformed seed or the transformed plant is substantially unaffected by the herbicidal composition,
  wherein the plant comprises:
    (1) a first gene that is functional in a plant, wherein the first gene comprises a nucleotide sequence that encodes a prephenate dehydrogenase, and
    (2) a second gene that is functional in a plant, wherein the second gene comprises a nucleotide sequence that encodes a p-hydroxyphenylpyruvate dioxygenase, and wherein the plant overexpresses the prephenate dehydrogenase and the p-hydroxyphenyl-pyruvate dioxygenase, and
    wherein said plant is cultivated in the presence of an amount of said inhibitor that is toxic to or decreases the growth of plants transformed with said second gene alone.

6. The method of claim 5, wherein said prephenate dehydrogenase is a yeast prephenate dehydrogenase.

7. The method of claim 5, wherein said p-hydroxyphenylpyruvate dioxygenase is a plant p-hydroxyphenylpyruvate dioxygenase.

8. A method for increasing the tolerance of a plant to an inhibitor of a p-hydroxyphenylpyruvate dioxygenase, the method comprising:
  cultivating a plant transformed with:
    (1) a first gene that is functional in a plant, wherein the first gene comprises a nucleotide sequence that encodes a prephenate dehydrogenase, and
    (2) a second gene that is functional in a plant, wherein the second gene comprises a nucleotide sequence that encodes a p-hydroxyphenylpyruvate dioxygenase, and wherein the plant overexpresses the prephenate dehydrogenase and the p-hydroxyphenylpyruvate dioxygenase, thereby increasing the tolerance of said plant to an inhibitor of a p-hydroxyphenylpyruvate dioxygenase, and
    wherein said plant is cultivated in the presence of an amount of an inhibitor of p-hydroxyphenylpyruvate dioxygenase that is toxic for to plants transformed with said second gene alone.

9. The method of claim 8, wherein said prephenate dehydrogenase is a yeast prephenate dehydrogenase.

10. The method of claim 8, wherein said p-hydroxyphenylpyruvate dioxygenase is a plant p-hydroxyphenylpyruvate dioxygenase.

11. A transformed plant or plant cell comprising:
  (1) a first gene that is functional in a plant or plant cell, wherein the first gene comprises a nucleotide sequence that encodes a yeast prephenate dehydrogenase, and
  (2) a second gene that is functional in a plant or plant cell, wherein the second gene comprises a nucleotide sequence that encodes a plant p-hydroxyphenylpyruvate dioxygenase,
  wherein the plant or plant cell overexpresses the prephenate dehydrogenase and the p-hydroxyphenylpyruvate dioxygenase and exhibits tolerance to an inhibitor of p-hydroxyphenylpyruvate dioxygenase, and
  wherein the concentration of prenylquinone in the plant or plant cell is higher than in a non-transformed plant or plant cell.

12. The plant or plant cell of claim 11, wherein the yeast is *Saccharomyces cereviseae*.

13. The plant of claim 11, wherein the plant p-hydroxyphenylpyruvate dioxygenase is from *Arabidopsis thaliana*.

14. A transformed plant or plant cell comprising:
  (1) a first gene that is functional in a plant or plant cell, wherein the first gene comprises a nucleotide sequence that encodes a prephenate dehydrogenase, and
  (2) a second gene that is functional in a plant or plant cell, wherein the second gene comprises a nucleotide sequence that encodes a p-hydroxyphenylpyruvate dioxygenase, and
  wherein the plant or plant cell overexpresses the prephenate dehydrogenase and the p-hydroxyphenylpyruvate dioxygenase.

15. The plant or plant cell of claim 14, wherein the first gene comprises the coding sequence of a yeast prephenate dehydrogenase gene.

16. The plant of claim 15, wherein the yeast is *Saccharomyces cereviseae*.

17. The plant of claim 14, wherein the second gene comprises the coding sequence of a plant p-hydroxyphenylpyruvate dioxygenase gene.

* * * * *